(12) United States Patent
Zeng

(10) Patent No.: US 6,770,306 B1
(45) Date of Patent: Aug. 3, 2004

(54) DRUGS FOR REDUCING VAGINAL ACIDITY AND TREATMENT OF VAGINITIS, AND THE USE THEREOF

(76) Inventor: Zhongming Zeng, Nanshan Hosp., Nantou, Shenzhen City, Guangdong (CN), 518052

( * ) Notice: Subject to any disclaimer, the term of this patent is extended or adjusted under 35 U.S.C. 154(b) by 0 days.

(21) Appl. No.: 09/674,062

(22) PCT Filed: Apr. 26, 1999

(86) PCT No.: PCT/CN99/00059

§ 371 (c)(1),
(2), (4) Date: Jan. 3, 2001

(87) PCT Pub. No.: WO99/55325

PCT Pub. Date: Nov. 4, 1999

(30) Foreign Application Priority Data

Apr. 26, 1998 (CN) ......................................... 98 1 08105

(51) Int. Cl.[7] .............................................. A01N 63/00
(52) U.S. Cl. ...................... 424/717; 424/93.45; 514/31; 514/254.07; 514/396; 514/399; 514/557; 514/738; 514/967
(58) Field of Search ........................ 424/93.45; 514/31, 514/254.03, 396, 399, 557, 738, 767

(56) References Cited

U.S. PATENT DOCUMENTS

| 4,937,234 A | | 6/1990 | Fahim | |
|---|---|---|---|---|
| 5,573,765 A | * | 11/1996 | Reinhard | ................. 424/93.45 |
| 5,858,974 A | * | 1/1999 | Little | .......................... 514/12 |

FOREIGN PATENT DOCUMENTS

EP  0 242 980 A2  10/1987

OTHER PUBLICATIONS

Notitification of Transmittal of International Preliminary Examination Report, Form PCT IPEA/416 (7,1992), dated Nov. 23, 2000, with translation.
International Preliminary Examination Report, Form PCT IPEA/409, dated Sep. 18, 2000, with translation.
Written Opinion, Form PCT/IPEA/408, dated Aug. 24, 2000, with translation.
Abstract JP880276052, Culture of Pseudomonas S:P Bacteria, dated May 11, 1990.

* cited by examiner

Primary Examiner—Christopher Tate
Assistant Examiner—Roy Teller

(57) ABSTRACT

The present invention relates to a pharmaceutical composition for reducing vaginal acidity, treating abnormal enhancement of vaginal acidity, and high acidity vaginitis associated with abnormal enhancement of vaginal acidity, especially for the treatment of fungal vaginitis, comprising of one or more ingredients defined as follows: amino acids, physiologically acceptable salts of amino acids, oligopeptides and polypeptides. Also, the present invention relates to the use of the said amino acids, physiologically acceptable salts of amino acids, oligopeptides and polypeptides, as active ingredients or auxiliaries in preparing drugs for reducing vaginal acidity, the treatment of abnormal enhancement of vaginal acidity, and high acidity vaginitis especially to their use in preparing drugs for the treatment of fungal vaginitis and the use thereof as nutrients for vaginal mucous membranes in preparing drugs that are locally applied in the vagina. It also relates to methods for reducing vaginal acidity, treatment of abnormal enhancement of vaginal acidity, and high acidity vaginitis associated with abnormal enhancement of vaginal acidity, and especially for treatment of fungal vaginitis.

9 Claims, No Drawings

DRUGS FOR REDUCING VAGINAL ACIDITY AND TREATMENT OF VAGINITIS, AND THE USE THEREOF

FIELD OF THE INVENTION

The present invention relates to a pharmaceutical composition for reducing vaginal acidity, treating abnormal enhancement of vaginal acidity, and high acidity vaginitis associated with abnormal enhancement of vaginal acidity, especially for the treatment of fungal vaginitis, comprising of one or more ingredients defined as follows: amino acids, physiologically acceptable salts of amino acids, oligopeptides and polypeptides. Also, the present invention relates to the use of the said amino acids, physiologically acceptable salts of amino acids, oligopeptides and polypeptides, as active ingredients or auxiliaries in preparing drugs for reducing vaginal acidity, the treatment of abnormal enhancement of vaginal acidity, and high acidity vaginitis especially to their use in preparing drugs for the treatment of fungal vaginitis and the use thereof as nutrients for vaginal mucous membranes in preparing drugs that are locally applied in the vagina It also relates to methods for reducing vaginal acidity, treatment of abnormal enhancement of vaginal acidity, and high acidity vaginitis associated with abnormal enhancement of vaginal acidity, and especially for treatment of fungal vaginitis.

BACKGROUND OF THE INVENTION

Fungal vaginitis, one of the common female vaginal diseases with a high morbidity rate, is difficult to effect a radical cure. In the U.S., more than 75% women suffer from fungal vaginitis at least once in their life, and about 5% of adult women suffer from repeated fungal vaginal infection, which is difficult to treat (Jack D. Sobel, MD. Candidal Vulvovaginitis, Clinical Obstetrics and Gynecology, 1993 Vol.36 (1): 153–165). The main clinical symptoms of these vaginal diseases include vulval pruritus, vaginal pain, leukorrhagia, dyspareunia, and urodynia. Therefore, this disease is harmful to the health of women as well as their life quality.

At present, for the treatment of fungal vaginitis, there are various anti-fungal drugs used to directly inhibit or kill fungi. The commonly used drugs include Ketoconazole, Fluconazole, mikostatin and Clotrimazolum, they can be administered locally in the vagina or taken orally. But most of the local vaginal anti-fungal agents contain starch and/or lactose as auxiliaries, for example as excipient. The present inventor has discovered that starch, lactose or other saccharides can significantly promote vaginal bacteria to produce acid, increase vaginal acidity, thus promoting fungal growth in the vagina, therefore the starch and/or lactose contained in the pharmaceutical composition is extremely unfavorable for the treatment of fungal infection in the vagina.

Currently, satisfactory effects cannot be achieved if sole anti-fungal drugs are used for the treatment of these vaginal diseases. For example, the treatment effect of the commonly used drugs such as, mikostatin, is generally 75–80%. A better effect can be achieved if glyoxaline anti-fungal drugs such as Ketoconazole, Treconazole, and Fluconazole, are used, which equates to about 85–90% (Jack D.Sobel). However, for many patients, the disease is often repeated after stopping the administration of the drug or during the next menstrual period, which makes it very difficult to effect any radical cure.

The object of the present invention is to provide a medicine for reducing vaginal acidity, treatment for abnormal enhancement of vaginal acidity, high acidity vaginitis and fungal vaginitis. This invention also relates to methods for treatment of abnormal enhancement of vaginal acidity, and high acidity vaginitis, especially for treatment of fungal vaginitis.

In order to seek a medicine which is effective in treating fungal vaginitis, the inventor conducted an extensive study, resulting in a simple formulation, which is easily used and applied. Utilizing Light Microscopy techniques, the inventor performed observations on vaginal secretions obtained from patients with fungal vulvovaginitis according to clinical diagnosis. It is difficult to determine the direct relationship between the clinical symptoms and fungal infection, because the inventor did not find fungi in the vaginal secretions in many of the patients examined. After further study however, the inventor achieved surprising results—for these cases the acidity in the vagina was abnormally higher (vaginal pH value <4.0) and a single case of high acidity can cause damage to vaginal mucous membranes, resulting in vaginitis. This therefore confirms that these cases actually relate more directly to abnormal enhancement of acidity in the vagina. The inventor calls these cases "high acidity vaginitis". The inventor also noticed that "high acidity vaginitis" has a close relationship with fungal vulvovaginitis, fungal vaginitis are accompanied with high acidity vaginitis. This is one of the main reasons why it is difficult to effect a radical cure for the repeated and stubborn fungal vaginitis by using only anti-fungal drugs. This discovery is of great significance because the inventor has set forth a new theory for the treatment of fungal vaginitis: namely, treatment for repeated and stubborn fungal vaginitis and correcting abnormal enhancement of vaginal acidity. This discovery is as important as the treatment with anti-fungal drugs, which will play an important role in raising the effect of the treatment for fungal vaginitis. The inventor corrected the abnormally-enhanced vaginal acidity and the diagnosed cases of fungal vaginitis by only using the medicine of the present invention, whereas any other anti-fungal drugs were not used. After treatment with the invention which involved correction of an abnormally-high acid environment in the vagina, the fungal infection disappeared, which is unimaginable before.

Clinically, sodium bicarbonate is used to clean the vagina to perform auxiliary treatment for fungal vaginitis. However, the mechanism of sodium bicarbonate solution has been commonly thought to change the microenvironment in the vagina and inhibit the growth of fungi. This is not the case that sodium bicarbonate solution changes the microenvironment in the vagina and inhibits the growth of fungi, as commonly known, but is that it decreases vaginal acidity temporarily. This method cannot reduce the acidity in the vagina and the treatment effect lasts for a short time, therefore, there is high acidity again in the vagina several hours after stopping the use of drugs.

The U.S. Pat. No. 4,804,674 teaches a method for enhancing sperm motility, wherein amino acids and/or salts of amino acids are used which can enhance sperm motility. These amino acids are mainly comprising aspartic acid, glutamic acid, arginine, histidine, asparagine, glutamine, and arginine aspartate. This patent does not indicate that the amino acids, oligopeptide and polypeptide can regulate vaginal bacterial metabolism, thus reducing the acid production in the vagina, nor does it indicate that vaginal acidity can be reduced by regulating vaginal bacterial metabolism. Also, the patent does not mention the relationship between abnormal enhancement of vaginal acidity and fungal vaginitis, or that amino acids, oligopeptide and polypeptide are used for reducing abnormal enhancement of vaginal acidity, treatment of high acidity vaginitis and fungal vaginitis.

The U.S. Pat. No. 4,937,234 discloses a pharmaceutical composition of neutral salts of gluconic acid, wherein zinc gluconate is an effective bacteriological component. Such amino acids as alanine, valine, isoleucine, proline, glycine, serine, threonine, asparagine, glutamine, lysine, arginine, histidine and mixtures thereof are also used as auxiliaries in the pharmaceutical composition of this patent, of which the main component is lysine. As shown in the examples 1 to 12 of the patent specification, the patent emphasizes that amino acids can regulate and change the acidity of the composition to neutral, and thus reduces the stimulation of the composition and enhances the sterilization of zine agents. This patent particularly emphasizes that its pharmaceutical composition can be used on the neonates, old people, eyes and noses that are sensitive to acid, for treatment of diaper rash, skin dryness and vaginitis. Although the patent mentions that the composition can treat vaginitis, it does not indicate what type of vaginitis the composition can treat, because completely different treatment methods and drugs are used for different types of vaginitis. Furthermore, no information or data indicates or suggests whether the lysine also exerts treatment effect on vaginitis when used separately. The inventor discovered that lysine is easily converted into toxic cadaverine in the vagina through bacterial metabolism, thus it is not suitable to administer lysine in a large amount into the vagina, particularly, it cannot be administered alone into the vagina, This patent does not indicate that the amino acids, oligopeptide and polypeptide can regulate vaginal bacterial metabolism thus reducing the acid production in the vagina, nor does it indicate that vaginal acidity can be reduced by regulating vaginal bacterial metabolism. Also, the patent does not mention the relationship between abnormal enhancement of vaginal acidity and fungal vaginitis, or that amino acids, oligopeptide and polypeptide are used for reducing abnormal enhancement of vaginal acidity, treatment of high acidity vaginitis and fungal vaginitis.

DESCRIPTION OF THE INVENTION

In order to seek a pharmaceutical composition which is effective in reducing vaginal acidity, the inventor has conducted an extensive study. Surprisingly, the inventor discovered that amino acids, salts of amino acids, oligopeptides and polypeptides can change the metabolic process of bacteria in the vagina and reduce vaginal acid production, and can be used to reduce vaginal acidity, a longer treatment effect was obtained compared to the treatment of directly using alkali substances. Based on his discovery and further study, the inventor completed the present invention.

The invention provides a pharmaceutical composition for reducing vaginal acidity and it is characterized by containing one or more components defined as follows: amino acids, physiologically acceptable salts of amino acids, oligopeptides and polypeptides; optionally containing pharmaceutically acceptable alkali substances; optionally, containing anti-fungal drugs of an effective amount; and one or more pharmaceutically acceptable carriers.

In the present invention, the said oligopeptides and polypeptides can be expressed by the following general formula:

Oligopeptide: An, n=1,2,/ . . . , 10;

Polypeptide: Am, m=11,12, . . . , 100;

In the above-mentioned general formula, A is an amino acid residue in a peptide chain; n and m are respectively the number of the amino acid residues in oligopeptide and polypeptide molecules. Peptide bond

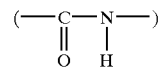

is used to effect the connection between amino acid residues.

Except stated especially, the amino acids mentioned in this specification include corresponding salts of amino acids. According to the invention, the amino acids in the said composition are formulations or combinations of many amino acids, especially it is a composition comprising compounds selected from the following groups: glutamic acid, alanine, aspartic acid, valine, isoleucine, proline, glycine, serine, threonine, glutamine, lysine, arginine, histidine, asparagine, methionine, phenylalanine, tyrosine, leucine, cysteine, tryptophane; preferably it is a composition comprising the compounds selected from the following group: glutamic acid, glutamine, aspartic acid, asparagine, isoleucine, phenylalanine, valine, threonine, leucine, and proline The acceptable physiological salts of amino acids mentioned in the invention are sodium salt, potassium salt, magnesium salt, calcium salt, or other salts of amino acids, preferably sodium salt.

With exception of glycine, all of the amino acids mentioned in the invention are L-type. The amino acids, oligopeptide and polypeptide can be hydrolysis products (such as tryptone, polypeptone, proteose peptone etc.) of varies kinds of proteins (such as muscular fibrin, hemoglobin, or casein) that are catalyzed by proteinases (such as pepsin, trypsin, or microbial proteinases), acids or alkalis, or the products (such as yeast extract, lactobacilli extract) from microbial fermentation substances rich in amino acids, oligopeptide and polypeptide, or amino acids or peptide agents available in markets. It is preferred to use the combination of many amino acids and/or their salts, especially the preferred amino acids or their salts. Alternatively, amino acids and/or their salts are mixed with oligopeptides and polypeptides. It is also preferred to directly use yeast extracts, tryptone, polypeptone or proteose peptone that containing plenty of amino acids, oligopeptides and polypeptides. However, the pharmaceutical composition of the invention may also contains minor kinds, of amino acids and/or salts of amino acids, especially the amino acids and/or salts of amino acids selected from the group defined as follows: glutamic acid, aspartic acid, valine, isoleucine, proline, threonine, phenylalanine, leucine. The composition containing only one or two sodium salts of amino acids can also party realize the object of the invention.

According to the invention specifications, the forms of the composition of the invention can be in the forms of lotion, drops, aerosol spray, suspension, emulsion, creams, tablets, effervescent tablets, suppository, gelate, unguentum, micro capsules, sustained release dosage, or any other acceptable vaginal local drug forms. The skilled in the art can mix amino acids, oligopeptides, polypeptides and other effective components with one or more pharmaceutical corners in a common method to prepare the pharmaceutical formulation described in this invention. The preferred form of the formulation of the invention is viscous gelate, and the preferred viscous, auxiliary base is Xanthan gum with a concentration ranging from 1.0%–2.5%. Xanthan gum has a high viscosity and is resistant to the changes of temperature and acidity or basicity. Xanthan gum can also keep the effective components in the composition uniformly contact with the vaginal mucous membranes and stay for a longer time to adjust acidity in the vagina.

According to different formulations of the pharmaceutical compositions of the invention, the total content of its amino acids can change within a wide range, and preferably is 30–350 mmol/L, but the particular preferred range is 80–200 mmol/L. When the composition also contains oligopeptides or polypeptides, the total content of amino acids, oligopeptides, and polypeptides can also change in a wide range, for example 0.5–15.0% (W/V), preferably 2–6% (W/V).

According to the invention, the amino acids, oligopeptides and polypeptides of the composition can be used as basic active components, and can realize the object of the invention when used separately with suitable pharmaceutical carriers.

According to the invention, the pharmaceutical composition can optionally contain the basic substances that are pharmaceutical and acceptable to the vagina, used for directly neutralizing the acid in vagina and can enhance the therapeutic effect of the composition of the invention. These basic substances are mainly meak-basic substances and salts of strong base and weak acids, such as calcium hydroxide, magnesium hydroxide, sodium carbonate, sodium bicarbonate, sodium lactate, Sodium Citrate, sodium acetate, calcium carbonate, potassium bicarbonate, sodium phosphate, disodium hydrogen phosphate, dipotassium hydrogen phosphate. The preferable basic substances are sodium carbonate, sodium bicarbonate, and sodium lactate.

The strong basic salts of amino acids, such as sodium salt or potassium salt, have strong basicity, so the composition containing only one or two sodium salts of amino acid also can realize the object of the invention.

According to the invention, the composition of the invention can also selectively contain anti-fungal drug of effective amount, used for directly suppressing and killing fungi, and enhance the treatment effect of the composition of the invention for fungal vaginitis. The examples of anti-fungal drugs are Ketoconazole, Treconazole, Itraconazole and Fluconazble, as well as nucleotide drugs such as 5-Flucytosine.

According to the invention, the composition of the invention can also selectively contain natural pharmaceutical plant extracts, for example the extracts of Radix Sophorae Flavescentis, Monnieri Fructus Cnidii, Herba Hedyotis Diffusae, Desmodium styracifolium, and Cortex Phellodendri, etc.

The weight/volume content (W/V) mentioned in the context of this application refers to grams of the specified component in 100 milliliter of the composition. In liquid compositions, amino acids or peptide components can be dissolved or suspended in one kind or more kinds of pharmaceutical carriers, and the undissolved components can be dissolved slowly when administered in the vagina.

The composition of the invention can be formulated by using the method known to the person skilled in the art For example, when the formulation is prepared in the form of a viscous gelate, thoroughly mix the effective components such as varies kinds of amino acids and yeast extract powder with viscous auxiliaries homogeneously, Then add distilled water to the mixture and stir it until the active components are dissolved and viscous auxiliaries swollen into a viscous gel, then add basic component, adjust pH value to 4.0–8.0, and finally carry out sterilization, either high-pressure or discontinuous sterilization methods can be used.

When suppositories, tablets, effervescent tablets, or capsules are used for the preparation of the composition, amino acids, oligopeptides, or polypeptides and/or basic substances and/or anti-fungal drugs and/or extracts of natural medicines can be mixed with other pharmaceutical carriers, granulating, tabletting, or filling in capsules. However, the above-mentioned composition contains no or little starch or other saccharides.

The present invention also relates to the use of the above-mentioned amino acids, oligopeptides or polypeptides as active components or auxiliary substances in the preparation of the pharmaceutical composition for reducing vaginal acidity, treating an abnormal increase of vaginal acidity and high acidity vaginitis, especially fungal vaginitis, and as nutrients of the cells of vaginal mucous membrane in the preparation of vaginal local composition.

The drugs described in the medicine preparation of this invention can be used to reduce vaginal acidity, treat abnormal increase of vaginal acidity (pH of vaginal secretions <4.0) and high acidity vaginitis, especially fungal vaginitis. These drugs also can be used as auxiliary substances for anti-fungal agents when locally administered into the vagina, or used as excipient in stead of starch, lactose and other saccharides to eliminate any negative effect causing abnormal increase of vaginal acidity, thus enhancing the treatment effect.

Amino acids are also used as nutrients for preparing the therapeutic agent for local administration into the vagina, or otherwise for sanitation and healthcare drugs, promoting the nutrition and renovation of the epithelial cells of vaginal mucous membrane.

The experiments in-vitro or in-vivo shows that the composition of this invention can effectively change vaginal bacterial metabolism, reduce the acidic metabolites thus reduce vaginal acidity. Therefore, it can be used for treating an abnormal increase of vaginal acidity, and high acidity vaginitis, especially fungal vaginitis.

This invention also relates to a method for reducing vaginal acidity, treating an abnormal increase of vaginal acidity, and high acidity vaginitis, especially fungal vaginitis, it includes providing patients with the above-mentioned drugs of this invention at the dosage required for effective therapy, if necessary.

The pharmaceutical composition and the method of this invention is administered locally into the vagina. For example, the composition in the form of effervescent tablets can be placed directly into the vagina, or daub or wash the vagina with the agent after it is dissolved in water or other suitable solvents. The composition of this invention in the form of viscous gelate can be administered directly into the vagina. The composition of this invention in the form of a solution can also be used to soak intravaginal tampons and then place the soaked tampon inside the vagina of the patient. The compositions of this invention in the forms of lotion, drop, aerosol spray, tablets (not containing starch or saccharides), suppository and capsule can be directly administered into vagina.

For the composition or method of his invention, the total .dosage of amino acids, oligopeptides or polypeptides, as active components per day, can change in a wide range. The preferred amount is 0.01–1.5 g, but the more preferred amount is 0.1–1.0 g, administered in one or more times, e.g. three times a day.

During the treatment wit the composition of this invention, observe the clinical symptoms of the patient and inspect the change of vaginal pH value every day. If possible, a smear dyeing assay should be performed on vaginal secretions to ascertain the change of bacterial flora and adjust he dosage and treatment time based on the changes of the illness, When the symptoms of the patient disappear or are alleviated, with the vaginal pH value remaining between 4.4 and 4.6, the drug administration should be stopped, or reduce its amount or only administered in a slight amount.

As for the method of this invention, the patient can be administered with the composition only containing the amino acid, oligopeptides and polypeptides of this invention as active components. Alternatively, the patient can be administered with the composition containing the amino acid, oligopeptides, polypeptides and basic substances of this invention as active components, or with the composition containing the amino acid, oligopeptides, polypeptides, basic substances and anti-fungal agents of this invention, or with the anti-fungal agents containing amino acids, oligopeptides and polypeptides of this invention as auxiliary components. Selectively, the composition containing only the amino acids, oligopeptides and polypeptides of this invention can be applied with suitable drugs containing basic substances and/or anti-fungal drugs. The composition of this invention can be administered at the same time as or different from basic substances and/or anti-fungal drugs, with no strict requirement in respect of the administration order, provided that the second drug is applied before the effect of first drug does not disappear.

After application of above-mentioned drugs, the clinical symptoms of the patient can be alleviated quickly, with the vaginal pH value raised to above 4.0 and the amount of fungi in the vagina reduced.

For the cases of abnormally-high vaginal acidity, the patient can be treated with the medicine of this invention until the symptoms are alleviated and the vaginal pH value remains steadily between 4.4–4.6. When the desired pH is reached, then the administration dosage can be reduced or ceased. For the cases with typical fungal vaginitis, in particular for repeated and stubborn fungal vaginitis, the patient can be treated with the composition of this invention containing anti-fungal agents until the symptoms are alleviated and the vaginal pH value remain steadily between 4.4–4.6, then the administered dosage can be reduced or ceased.

BEST EXECUTION METHOD OF THIS INVENTION

This invention will be described in more details by providing the following examples. It should be understood however, that these examples are only for the illustration of this invention; not to impose any restrictions on his invention. All the variants or modifications, which are made based on the principle of this invention shall be deemed to be included in this invention.

COMPOSITION EXAMPLE

Example 1

Composite amino acids of 3.0 g (glutamic acid, aspartic acid, isoleucine, methionine, phenylalanine, tyrosine, valine, leucine, proline of 2.36 mmol each), yeast extract powder of 1.0 g, sodium bicarbonate of 1.0 g and Xanthan gum of 1.6 g are nixed homogeneously, and 100 ml of distilled water is added into the mixture, stirred until all of the components are dissolved, and Xanthan gum swells in the form of homogeneous viscous gum, and then sterilize.

Example 2

100 ml of the composition in the following formulation was prepared substantially according to the method as described in Example 1:

Tryptone 5.0 g, Xanthan gum 1.6 g, and distilled water q.s.

Example 3

100 ml of .the composition in the following formulation was prepared substantially according to the method as described in Example 1.

Yeast extract powder 3.0 g, sodium lactate 1.5 g, Ketoconazole 2.0 g, Xanthan gum 1.8 g, and distilled water q.s.

Example 4

3.0 g of yeast extract powder, 1.0 g of sodium bicarbonate, and 1.6 g of Xanthan gum were mixed homogeneously. Then 100 ml of distilled water was added in the mixture while stirring in order to dissolve the yeast powder and sodium bicarbonate and the Xanthan gum is swollen to homogeneous viscous gum, and then sterilized.

Example 5

100 ml of the composition in the following formulation was prepared substantially according to the method as described in Example 1.

0.5 mmol each of the following amino acids: glutamic acid, alanine, aspartic acid, valine, isoleucine, proline, glycine, serine, threonine, lysine, arginine, histidine, methionine, phenylalanine, tyrosine, leucine, cysteine, tryptophane, oxyproline, cystine, ornithine; yeast extract powder 1.0 (W/V); sodium bicarbonate 1.0% (W/V); Xanthan gum 1.6% (W/V); water q.s.; and dispensing agent pH8.3.

Example 6

100 ml of the composition in the following formulation was prepared substantially according to the method as described in Example 1.

1.0 mmol each of the following amino acids: glutamic acid, aspartic acid, isoleucine, proline, methionine, phenylalanine, tyrosine, valine and leucine; 2.0% (W/V) yeast extract powder, 1.5% sodium lactate (W/V); 1.5% (W/V) Xanthan gum; water q s. The pH value of the composition was adjusted to 6.5.

Example 7

0.17 mmol each of the following amino acids: glutamic acid, alanine, aspartic acid, valine, isoleucine, proline, glycine, serine, threonine, lysine, arginine, histidine, methionine, phenylalanine, tyrosine, leucine, cysteine, and tryptophane;

| | |
|---|---|
| Sodium bicarbonate | 1.0 g; |
| Ketoconazole | 2.0 g; |
| Xanthan gum | 1.6 g; |
| Distilled water | q.s. |

Example 8

100 ml of the composition in the following formulation was prepared substantially according to the method as described in Example 1.

1.5 mmol each of the following amino acids: glutamic acid, glutamine, aspartic acid, asparagine, valine, isoleucine, proline, threonine, phenylalanine, leucine;

0.5 mmol each of the following amino acids: methionine, alanine, glycine, serine, lysine, arginine, histidine, tyrosine, cysteine, and tryptophane;

| | |
|---|---|
| Xanthan gum | 1.6 g; |
| Distilled water | q.s. |

Example 9

100 ml of the composition in the following formulation was prepared substantially according to the method as described in Example 1.

1.5 mmol each of the following amino acids: glutamic acid, glutamine, aspartic acid, asparagine, valine, isoleucine, proline, threonine, phenylalanine, and leucine;

0.2 mmol each of the following sodium salts of amino acids: sodium salt of methionine, sodium salt of tyrosine, sodium salt of cysteine, sodium salt of alanine, sodium glycinate, sodium salt of serine, sodium salt of lysine, sodium salt of arginine, sodium salt of tryptophane, and sodium salt of histidine.

| | |
|---|---|
| Itraconazole | 2 g; |
| Yeast extract powder | 0.8 g; |
| Xanthan gum | 1.6 g; |
| Distilled water | q.s. |

Example 10

100 ml of the composition in the following formulation was prepared substantially according to the method as described in Example 1.

1.0 mmol each of the following amino acids: glutamic acid, glutamine, aspartic acid, asparagine, valine, isoleucine, proline, threonine, phenylalanine, and leucine;

0.1 mmol each of the following sodium salts of amino acids; sodium salt of methionine, sodium salt of tyrosine, sodium salt of cysteine, sodium salt of alanine, sodium glycinate, sodium salt of serine, sodium salt of lysine, sodium salt of arginine, sodium salt of tryptophane, and sodium salt of histidine.

Potassium chloride 0.5 mmol, magnesium chloride 0.16 mmol riboflavin 0.2 ppm, thiamine 0.2 ppm, nicotinic acid 0.2 ppm, calcium pantothenate 0.2 ppm Fluconazole 2 g; Xanthan gum 1.6 g;

Example 11 (lotion)

100 ml of lotion of this invention was prepared in the following formulation;

1.0 mmol each of the following amino acids: glutamic acid, aspartic acid, valine, isoleucine, proline, threonine, phenylalanine, and leucine;

0.3 mmol each of alanine, glycine, serine, tyrosine, cysteine, tryptophane and methionine.

Water q.s.

Example 12 (lotion)

100 ml of the lotion of this invention was prepared in the following formulation.

1.0 mmol each of valine, isoleucine, proline, threonine, phenylalanine, and leucine;

1.0 mmol each of sodium glutamate and sodium aspartate;

0.2 mmol each of methionine, alanine, glycine, serine, cysteine, tyrosine, tryptophane, and lysine;

0.1 mmol of adenine, guanine, uracil, and cytosine;

200 mg of Vitamin C;

100 ml of extract of natural herbs: 30 g each of Radix Sophorae Flavescentis, Monnieri Fructus Cnidii and Herba Hedyotis Diffusae, and sink the mixture in 250 ml of water at a temperature from 90–100° C. for 40 minutes, and then filtrate the residue and obtain the extract of the herb.

Example 13

100 ml of lotion of this invention was prepared in the following formulation 1.0 mmol each of isoleucine, valine, proline, threonine; sodium salt of leucine, sodium glutamate, sodium aspartate, sodium salt of phenylalanine;

150 mg of yeast extract powder;

1.5 g of Clotrimazole

Water q.s.

Example 14 (Composition in Capsules)

The materials of amino acids are mixed homogeneously in the following formulation, and then packed into capsules, with each capsule containing a total weight of 0.5 g of amino acids sodium salt of amino acids, and 50000 units of mikostatin:

1.0 mmol each of valine, isoleucine, proline, feminine, phenylalanine, leucine, glutamic acid, and aspartic acid;

150 mg of yeast extract powder;

and 120000 units of mikostatin (Note: the total weight of the above-mentioned amino acids and oligopeptide, etc. is about 1200 mg)

Example 15 (Composition in Suppository)

By using glycerin and gelatin as substrate (the proportion of water, gelatin and glycerin is water: gelatin: glycerin= 10:20:70), the composition in the form of suppository in the following formulation was prepared according to the method known to the skilled in the art, with each suppository containing a total amount of 0.5 g of amino acids/sodium salt thereof and 0.1 g of miconazole.

1.0 mmol each of valine, isoleucine, proline, threonine, phenylalanine, leucine, sodium glutamate, and sodium aspartate;

150 mg of yeast extract powder;

0.24 g of miconazole

Substrate for suppository.

Example 16 (Composition in the Form of Unguentum)

By using glycerin and gelatin as the substrates (10–30% of glycerin and 1–3% of gelatin), the composition in the following formulation in the form of unguentum was prepared according to the method known to the skilled in the art:

1.0 mmol each of valine, isoleucine, proline, threonine, phenylalanine, leucine, glutamic acid, and aspartic acid;

150mg of yeast extract powder;

12 g of unguentum substrate.

Example 17 (Composition in the Form of Tablets)

By using Xanthan gum or gelatin as adhesive, and sodium bicarbonate as disintegration agent, magnesium stearate as lubricant, the composition in the form of effervesce tablets in the following formulation was prepared according to the method known to the skilled in the art. Each tablet contains a total weight of 0.5 g of amino acids, oligopeptides and polypeptides as well as 0.1 g of Ketoconazole. Note that no sugar or starch is added;

1.0 mmol each of valine, isoleucine, proline, threonine, phenylalanine, leucine, glutamic acid, and aspartic acid;

150 mg of yeast extract powder;

a 0.24 g of Ketoconazole.

Example 18 (Composition in Capsules)

The amino acids are used in the following formulation, and packed into: the capsules after being mixed homogeneously, with each capsule containing 0.5 g of sodium glutamate and 50000 units of mikostatin:

| | |
|---|---|
| Sodium glutamate | 500 g |
| mikostatin | 50,000,000 units |

Example 19 (Composition in Suppository)

By using glycerin and gelatin as substrate (the proportion of water to gelatin to glycerin is 10.20:70), composition in the form of suppository in the following formulation was prepared according to the method known to the skilled in the art, with each suppository containing sodium glutamate and sodium aspartate of 0.25 g each and miconazole of 0.1 g:

| | |
|---|---|
| Sodium glutamate | 250 g |
| Sodium aspartate | 250 g |
| Miconazole | 100 g |
| Suppository substrate | |

Example 20

100 ml of the composition in the following formulation was prepared substantially according to the method as described in Example 1.

1.0 mmol each of the following sodium salt of amino acids: sodium glutamate sodium aspartate, sodium of isoleucine, sodium salt of phenylalanine, sodium salt of valine, sodium salt of leucine, sodium salt of proline, and sodium salt of threonine;

0.1 mmol each of the following sodium salts of amino acids: sodium salt of methionine, sodium salt of tyrosine, sodium salt of cysteine, sodium salt of alanine, sodium glycinate, sodium salt of serine, sodium salt of lysine, sodium salt of arginine, sodium salt of tryptophane, and sodium salt of histidine.

Potassium chloride 0.5 mmol, magnesium chloride 0.16 mmol

Adenine 0.2 mmol, guanine 0.2 mmol, uracil 0.2 mmol, and cytosine 0.1 mmol;

riboflavin 0.2 ppm, thiamine 0.2 ppm, nicotinic acid 0.2 ppm, calcium pantothenate 0.2 ppm Xanthan gum 1.6 g;

Distilled water q.s.

The effectiveness of the composition or method of this invention is illustrated by the following experimental examples:

TYPICAL CASE REPORT

Experimental Example 1

Case 1, female, 32 years old, suffering from vaginal pruritus, accompanying pains for two years, severe before menstruation and alleviated after menstruation, diagnosed with repeated fungal vaginitis. After treatment with antifungal drugs and washing the vagina, her illness improved, but she suffered from the illness again after the medication was ceased. The inventor performed an inspection on her vaginal secretion and the test result of its pH value was less than 3.8, the vaginal smear indicated fungal spores, so the patient was diagnosed with "high-acidity vaginitis and accompanying fungal vaginitis". 3 ml of the composition of this invention (shown in Example 1) was administered twice a day. After application of the drug for one day, the symptoms were alleviated substantially and the secretion quantity was reduced. After application of the drug for three days, pruritus vulvae disappeared and test results of vaginal secretion revealed pH 4.4, and the smear dyeing indicated that there were no fungal spores. The patient did not take the medication any more, and the pH value in the vagina was less than 4.0, again, two weeks after menstruation, with the symptoms substantially alleviated than prior to treatment. Therefore 1 ml of the composition of this invention was used again, twice a day until the symptoms disappear. Such treatment continued for three weeks and afterwards the patient never suffered from the illness.

Experimental Example 2

Case 2, female, 30 years old, suffered from pruritus vulvae and leukorrhagia accompanyed with dyspareunia for more than one year. The patient had pruritus vulvae and pains with a feeling of burning, especially before menstruation, feeling anxious accompanying leukorrhagia and dyspareunia. This patient was diagnosed with fungal vaginitis. Effervescent tablets containing miskostatin and ketoconazole Cream was administered locally into the vagina with fluconazole taken orally. During the use of the drugs the symptoms were alleviated substantially, but after ceasing administration of the drugs, or after menstruation, the illness returned slowly and became more severe. The inventor performed inspection on her vaginal secretions which revealed a pH value of less than 3.8, the vaginal smear dyeing showed no fungal spores and fungal filaments, and a diagnosis of "high-acidity vaginitis" was made. The patient was treated with the composition of this invention (as shown in Example 2) with 4 ml of the composition administered twice a day. After application of the drug for one day, pruritis vulvae was alleviated substantially and the leukorrhagia was reduced, with analysis of vaginal secretions showing a pH value of 4.0. After application of the drug for three days, vaginal secretion was pH 4.4. Such treatment continued with reduced quantity, and after two months, the illness was cured completely, and the patient never suffered from the illness again.

Experimental Example 3

Case 3, female, 28 years old, suffered from pruritus vulvae, pains with a feeling of burning and leukorrhagia accompanyed with coagulate like bean curd for more than half year. The patient was diagnosed "fungal vaginitis." The treatment with anti-fungal drags may control the symptoms, but the administration can not be ceased. The inventor performed an inspection, the pH of her vaginal secretions is less than 3.8, there are many fungal filaments in the vaginal secretions. The patient was administrated with the composition of this invention (as shown in example 3), with 3 ml twice a day. Two days later, pruritis vulvae and pain were alleviated significantly, the leukorrhagia was reduced, the coagulate like bean curd was disappeared. Investigations indicated that the vaginal acidity was reduced and pH value of the secretion was 4.0, and there was no fungi. The drug was applied until the pH value of vaginal secretion was 4.4.

Experimental Example 4

Case 4, female, 38 years old, suffered from repeated pruritis vulvae for more than one year, severe before menstruation and alleviated after menstruation. The inventor investigated the vaginal secretion and found its pH value is 3.8, the smear dyeing found no fungal spores, and a diagnosis of "high-acidity in vagina accompanying fungal infection" was made. The composition of this invention (shown in Example 8) was administered twice a day with 3 ml being administered each time. After application of the drug for one day, the symptoms were alleviated substantially and the vaginal secretion quantity was reduced. After application of the drug for three days, pruritus vulvae disappeared and investigations revealed that the pH of vaginal secretion was pH 4.4, the smear dyeing indicated no fungal spores. The patient ceased taking the drug.

Experimental Example 5

Case 5, female, 27 years old, suffered from repeated pains with a feeling of burning in her vulvae, accompanied with coagulate like bean curds for half a year. The inventor examined this lady and found that the pH of her vaginal secretions is <3.8, there was no fungal spores and filaments in the secretion. She was treated with the composition of this invention (shown in Example 11), twice a day with 10 ml administered at each time. After application of the drug for three days, the pruritis with other symptoms were significantly reduced. Also, leukorrhagia was reduced, without coagulate residues like bean curd, the pH value of the vaginal swab was 4.0 and no fungi was found. This treatment outcome resulted in the dosage being reduced to once a day. After two days, the vaginal swab was examined, pH=4.4, the medication was ceased.

Experimental Example 6

Experiment in vitro:

Experimental Method:

(1) The preparation of the composition: yeast extract powder and Xanthan gum were respectively used to prepare the following compositions according to the method mentioned above. In order to evaluate its own effect of the protein hydrolysis products on the acidity production of vaginal bacteria when it is separately used, no sodium lactate or sodium bicarbonate was added in this experimental composition, and 1% of maltose was added as carbon source.

A. yeast tract powder 1.0% (W/V), maltose 1% (W/V), Xanthan gum 1.6% (W/V), pH6.7
B. yeast extract powder 5.0% (W/V), maltose 1% (W/V), Xanthan gum 1.6% (W/V), pH6.7

The above-mentioned compositions were filled into tubes after sterilization with each tube containing 5 ml, ready for use.

(2) The preparation of the specimen suspension: vaginal secretion was taken by a cotton swab from one of the patients with vaginal secretions of pH value less than 4.0. Then the swab was washed in 2 ml sterilized Trypcase-soy Broth immediately, and thus the specimen suspension was ready. The vaginal secretion smear dyeing showed that there are many Gram-positive bacilli, positive cocci and Gram-negative bacilli are little.

(3) The above-mentioned specimen suspension was inoculated immediately into the tubes containing the above-mentioned composition, 10 ul for each tube, mixed homogeneously. The tubes were placed in a candle jar for cultivation, at 37° C., under anaerobic conditions. The pH value of the culture solution was measured after 10 hours and 24 hours respectively and a smear test was performed.

Result: as shown in the table, the composition of this invention containing 1.0% yeast extract powder had no substantial inhibition on the acidity production of vaginal bacteria. After cultivation of 10–24 hours, the pH value of the culture was decreased to 4.1; however, the composition of this invention containing 5.0% yeast extract powder had substantial inhibition on the acidity production of vaginal bacteria After cultivation of 10–24 hours, the pH value of the culture was decreased to 5.1.

| Yeast extract contained in composition (%) | bacteria in specimen suspension | pH of the composition | 10 hours culture pH bacteria | 24 hours culture pH bacteria |
| --- | --- | --- | --- | --- |
| 1% | G + b | 6.7 | 6.5 G + b | 4.1 G – b, G + c |
| 5% | G + b | 6.7 | 6.5 G – b | 5.1 G + c, G – b |

Conclusion: the yeast extract powder contains abundant of amino acids, oligopeptide, and other protein hydrolytic products and vitamins. In this experiment, the composition of this invention containing a substantial amount of yeast extract had a suppression action on the acid production, even the growth of Gram-positive bacilli in vagina, which showed that amino acids, oligopeptide and protein hydrolytic products can reduce the acid production of the bacteria in the vagina.

Industrial Application

Based on the discovery that the high acid environment in the vagina per se can cause "high-acidity vaginitis" and possibly induce fungal vaginitis, this invention put forward a completely-new treatment concept for fungal vaginitis and high-acidity vaginitis. Compared with current treatment methods for fungal vaginitis, the composition of this invention has a higher treatment effect and cure rate, even the composition of this invention containing no anti-fungal agents can cure some of the vaginal fungal infections, which is unthinkable for existing technology.

What is claimed is:

1. A method of treating the abnormally high acidity in the vagina, comprising:
    providing a pharmaceutical formulation consisting essentially of an effective amount of a composition of amino acids, wherein the said composition comprising the following amino acids and/or physiologically acceptable salts thereof: glutamic acid, aspartic acid, isoleucine, phenylalanine, valine, leucine, proline and threonine, a sufficient amount of pharmaceutically acceptable acid or alkali, which results in a pH of the composition from 4.0–8.0, and or more pharmaceutical carriers;

determining whether the vagina, pH value is less than 4.0; and if the vaginal pH value is less than 4.0, administering said pharmaceutical composition vaginally.

2. A method for treating vaginitis in which the acidity level of the vagina is abnormally high comprising:

providing a pharmaceutical formulation consisting essentially of an effective amount of a composition of amino acids, wherein the said composition comprising the following amino acids and/or physiologically acceptable salts thereof: glutamic acid, aspartic acid, isoleucine, phenylalanine, valine, leucine, proline and threonine, a sufficient amount of pharmaceutically acceptable acid or alkali, which results in a pH of the composition from 4.0–8.0, and one or more pharmaceutical carriers;

determining whether the vaginal pH value is less than 4.0; and if the vaginal pH value is less than 4.0, administering said pharmaceutical composition vaginally.

3. A method for treating fungal vaginitis in which the acidity level of the vagina is abnormally high comprising:

providing a pharmaceutical formulation consisting essentially of an effective amount of a composition of amino acid, wherein the said composition comprising the following amino acids and/or physiologically acceptable salts thereof: glutamic acid, aspartic acid, isoleucine, phenylalanine; valine, leucine, proline and threonine, a sufficient amount of pharmaceutically acceptable acid or alkali, which results in a pH of the composition from 4.0–8.0, and one or more pharmaceutical carriers;

determining whether the vaginal pH value is less than 4.0; and if the vaginal pH value is less than 4.0, administering said pharmaceutical composition vaginally.

4. The method according to claim 1, 2 or 3 wherein the said composition of amino acids in said pharmaceutical formulation further comprises one or more of the following amino acids and/or physiologically acceptable salts thereof: methionine, tyrosine, cysteine, alanine, glycine, serine, lysine, glutamine, asparagine, arginine, tryptophane and histidine.

5. The method according to claim 1, 2, or 3 further comprising providing said pharmaceutical formulation in the form of viscous gels, lotion, tablets, effervescent tablets, suppositories, emulsion, ointments or micro-capsules.

6. The method according to claim 5, further comprising providing said pharmaceutical formulation in the form of a viscous gel, lotion or emulsion, wherein the total content of amino acids and/or the pharmaceutically acceptable salts thereof is in the range of 30–35 mmol/L.

7. The method according to claim 6, wherein the total content of amino acids and/or the physiologically acceptable salts thereof is in the range of 80–200 mmol/L.

8. The method according to claim 1, wherein the said physiologically acceptable salts of amino acids is the sodium salt, potassium salt, calcium salt or magnesium salt of amino acids.

9. The method according to claim 8, wherein the said physiologically acceptable salt of amino acid is the sodium salt of amino acid.

* * * * *

UNITED STATES PATENT AND TRADEMARK OFFICE
CERTIFICATE OF CORRECTION

PATENT NO. : 6,770,306 B1 Page 1 of 1
APPLICATION NO. : 09/674062
DATED : August 3, 2004
INVENTOR(S) : Zhongming Zeng It is certified that error appears in the above-identified patent and that said Letters Patent is hereby corrected as shown below:

In the claims:

In Claim 6, delete "30-35 mmol/L" insert --30-350 mmol/L--.

Signed and Sealed this

Twenty-eighth Day of November, 2006

JON W. DUDAS
*Director of the United States Patent and Trademark Office*